United States Patent [19]

Aoyama et al.

[11] Patent Number: 5,679,875

[45] Date of Patent: Oct. 21, 1997

[54] METHOD FOR MANUFACTURING 1,1,1,2,3-PENTAFLUOROPROPENE 1,1,1,2,3-PENTAFLUOROPROPANE

[75] Inventors: Hirokazu Aoyama; Eiji Seki, both of Settsu, Japan

[73] Assignee: Daikin Industries, Ltd., Osaka, Japan

[21] Appl. No.: 338,528

[22] PCT Filed: May 19, 1993

[86] PCT No.: PCT/JP93/00661

§ 371 Date: Nov. 30, 1994

§ 102(e) Date: Nov. 30, 1994

[87] PCT Pub. No.: WO93/25510

PCT Pub. Date: Dec. 23, 1993

[30] Foreign Application Priority Data

| Jun. 5, 1992 | [JP] | Japan | 4-171949 |
| Jun. 12, 1992 | [JP] | Japan | 4-179106 |
| Sep. 4, 1992 | [JP] | Japan | 4-262865 |
| Sep. 4, 1992 | [JP] | Japan | 4-262866 |
| Dec. 29, 1992 | [JP] | Japan | 4-360966 |

[51] Int. Cl.$^6$ ............... C07C 21/18; C07C 19/08
[52] U.S. Cl. ............... 570/156; 570/157; 570/158; 570/175
[58] Field of Search ............... 570/156, 157, 570/158, 175

[56] References Cited

U.S. PATENT DOCUMENTS

| 2,461,523 | 2/1949 | Coffman et al. | 570/156 |
| 2,599,631 | 6/1952 | Harmon | 570/156 |
| 2,695,320 | 11/1954 | Hedrick | 570/157 |
| 5,059,729 | 10/1991 | Gervasutti | 570/175 |

FOREIGN PATENT DOCUMENTS

| 234012 | 9/1987 | European Pat. Off. | 570/156 |
| 4-311202 | 5/1968 | Japan | 570/157 |

Primary Examiner—C. Warren Ivy
Assistant Examiner—Lyman H. Smith
Attorney, Agent, or Firm—Armstrong, Westerman, Hattori, McLeland & Naughton

[57] ABSTRACT

The present inventions provide manufacturing methods of 1,1,1,2,3-pentafluoropropene characterized by the reaction of removing HF by means of the contact of 1,1,1,2,3,3-hexafluoropropane in the gas state with active carbon or active carbon added with metallic salt. 1,1,1,2,3-pentafluoropropene can be produced from easily available 1,1,1,2,3,3-hexafluoropropane by cost-effective industrial methods at high yields according to these inventions.

The inventions also provide manufacturing methods of 1,1,1,2,3-pentafluoropropane characterized by reducing 1,1,1,2,3-pentafluoropropene with hydrogen under the presence of a hydrogenation catalyst consisting of palladium added with one or more of silver, copper, gold, tellurium, zinc, chromium, molybdenum, and thallium or under the presence of a rhodium catalyst. The desired product can be produced at high reactivities and high selectivities according to these inventions.

20 Claims, No Drawings

METHOD FOR MANUFACTURING 1,1,1,2,3-PENTAFLUOROPROPENE 1,1,1,2,3-PENTAFLUOROPROPANE

SPECIFICATION

This application is the U.S. national stage filing of PCT/JP93/00661 filed May 19, 1993 published as WO/93/25510 on Dec. 23, 1993.

FIELDS OF INDUSTRIAL APPLICATION

The present inventions relate to methods for manufacturing 1,1,1,2,3-pentafluoropropene, which is useful as an intermediate for compounds that can be substitutes for CFC and HCFC as refrigerants, blowing agents and cleaning agents, and as a monomer of macromolecule compounds, and methods for manufacturing 1,1,1,2,3-pentafluoropropane, which is a useful compound that can be said substitutes for CFC and HCFC for said uses.

CONVENTIONAL METHODS

Among the conventionally known manufacturing methods of 1,1,1,2,3-pentafluoropropene are: 1) the method of 1,1,1,2,3,3-hexafluoropropane (which is produced by hydrogenating hexafluoropropene) being reacted with an aqueous solution of KOH with a 70% to 80% concentration at 150° C. (Ann. Chim. (Italy) vol. 55, 850p, 1965); and 2) the method of 1,1,1,2,3,3-hexafluoropropane being reacted with KOH in dibutylether (Izvest. Akad. Nauk S.S.S.R., Otdel. Khim. Nauk 1412p, 1960). Another known method is: the method of removing HF from 1,1,1,2,3,3-hexafluoropropane by means of granular KCl in the gaseous phase at 700° C. to produce the desired product (Ann. Chim. (Italy) vol. 55, 850p, 1965).

Those methods, however, contained in the above-mentioned literature are not cost-effective because a large amount of alkali is used. As to the gaseous reaction process with KCl it does not suit to the industrial production because it produces a 30% large amount of 1,1,1,3,3-pentafluoropropene having a boiling point approximate to that of 1,1,1,2,3-pentafluoropropene and being difficult to be separate by the ordinary rectification methods cannot well separate away.

The known manufacturing method of 1,1,1,2,3-pentafluoropropane is the method of hydrogenating 1,1,1,2,3-pentafluoropropene as a raw material (Izvest. Akad. Nauk S.S.S.R. 1960, 1412–18).

This method, however, has a low yield because it also further hydrogenates the material and produces 1,1,1,2-tetrafluoropropane. The method does not suit to the industrial production because 1,1,1,2-tetrafluoropropane, which is azeotropic or pseudo-azeotropic with 1,1,1,2,3-pentafluoropropane, is difficult to separate.

OBJECTIVES OF THE INVENTIONS

An objective of the present inventions is to provide a highly cost-effective industrial method to produce 1,1,1,2,3-pentafluoropropene at high yields.

The other objective of those inventions is to provide a method with high reactivities and selectivities to produce 1,1,1,2,3-pentafluoropropane.

CONTENTS OF THE INVENTIONS

The inventors have thoroughly studied cost-effective industrial production methods of 1,1,1,2,3-pentafluoropropene, particularly those by means of the reaction to remove hydrogen fluroride from 1,1,1,2,3,3-hexafluoropropane which is obtained by hydrogenating hexafluoropropene, which is easily available. As a result, they have discovered that the contact of 1,1,1,2,3,3-hexafluoropropane in the gaseous state with active carbon causes a reaction of removing HF to produce 1,1,1,2,3-pentafluoropropene at high yields. The first invention has been achieved based on this discovery.

That is, the first invention relates to a method for manufacturing 1,1,1,2,3-pentafluoropropene characterized by the creation of reaction to remove HF from 1,1,1,2,3,3-hexafluoropropane by means of the contact of 1,1,1,2,3,3-hexafluoropropane in the gaseous state with active carbon.

For the first invention, it is essential to make 1,1,1,2,3,3-hexafluoropropane in the gaseous state contact with active carbon. This is in practice a form of vapor phase reaction in which, for example, 1,1,1,2,3,3-hexafluoropropane in the gaseous state is made flow through a reaction tube filled with active carbon at a specific temperature. The methods of the vapor-phase reaction can be the fixed-bed reaction, the fluid-bed reaction and so on.

There are no particular restrictions in terms of kinds of active carbon to be used. A granular active carbon product, Shirasagi C, made by Takeda Yakuhin Kogyo Co., Ltd. and a coconut shell active carbon product, Yashicoal, made by Taihei Kagaku Sangyo Co., Ltd. can preferably be used.

The appropriate reaction temperature is 200° C. to 600° C. or more appropriately 250° C. to 500° C. The above-stated reaction does progress very little under that temperature range and can produce a large amount of unfavorable by-products over that range.

The contact time with active carbon can be largely varied, but it is ordinarily 0.1 second to 200 seconds or more appropriately 0.5 second to 120 seconds.

There are various methods available to produce pentafluoropropane or 1,1,1,2,3-pentafluoropropane, which can be a substitute for CFC and HCFC, from 1,1,1,2,3-pentafluoropropene, which can be produced by means of the first invention.

An example of those methods is the hydrogenation reaction which is contained in Izvest. Akad. Nauk S.S.S.R., 1960, 1412–18. Another method to produce 1,1,1,2,3-pentafluoropropane with a higher yield is vapor-phase hydrogenation reaction with a palladium catalyst particularly at 30° C. to 450° C.

The methods of said vapor-phase reaction can be the fixed-bed reaction, the fluid-bed reaction and so on.

The palladium catalyst is preferably carried by at least one selected from active carbon, alumina, silica gel, titanium oxide and zirconia, or other carrier.

The particle size of the carrier is preferably 0.1 mm to 100 mm although it has little effect on the reaction.

The acceptable range of the carrying concentration is from 0.05% to 10%, but the normally recommended range is 0.5% to 5% by weight.

The reaction temperature is ordinarily 30° C. to 450° C. or more appropriately 70° C. to 400° C.

The ratio of hydrogen and the raw material in the 1,1,1,2,3-pentafluoropropene hydrogenation reaction can be largely varied. The reaction should, however, be ordinarily conducted with a stoichiometric amount of hydrogen with a minumum. An amount of hydrogen, such as 4 mol or more, which is far more than the stoichiometric one can be used for the whole mol of the starting material.

There are no restrictions on the reaction pressure so that the reaction can be conducted under a high pressure, a reduced pressure and the atmospheric pressure. It is preferable to conduct the reaction under a high pressure or the atmospheric pressure because the reduced pressure requires more complicated devices.

The contact time in the hydrogenation reaction is ordinarily 0.1 second to 300 seconds or more appropriately 1 second to 30 seconds.

The inventors have discovered that the contact of 1,1,1,2,3,3-hexafluoropropane in the gaseous state with active carbon added with metallic salt causes a reaction to remove HF to produce 1,1,1,2,3-pentafluoropropene at high yields. The second invention has been achieved based on this discovery.

That is, the second invention relates to a method for manufacturing 1,1,1,2,3-pentafluoropropene characterized by the reaction to remove HF from 1,1,1,2,3,3-hexafluoropropane by means of the contact of 1,1,1,2,3,3-hexafluoropropane in the gaseous state with active carbon added with metallic salt.

For the production method of the second invention, one or more kinds of metallic salt belonging to the element groups I, II, III, IV, V, VI, VII, VIII, IX, X, XI, XII, XIII, and XIV in accordance with the newly proposed periodic table by IUPAC in 1985 should be preferably added to active carbon to be used.

In this case, it is better to add at least one of metallic salts composed of potassium, silver, zinc, copper and magnesium to that active carbon for the above-mentioned use.

For the second invention, it is essential to make 1,1,1,2,3,3-hexafluoropropane in the gaseous state contact with active carbon added with the above-stated metallic salt. This is in practice a form of vapor phase reaction in which, for example, 1,1,1,2,3,3-hexafluoropropane in the gaseous state is made flow through a reaction tube filled with active carbon added with the metallic salt at a specific temperature. The methods of the vapor-phase reaction can be the fixed-bed reaction, the fluid-bed reaction and so on.

There are no particular restrictions in terms of kinds of active carbon to be used in the second invention. A granular active carbon product, Shirasagi C, made by Takeda Yakuhin Kogyo Co., Ltd. and coconut shell active carbon products, Yashicoal, made by Taihei Kagaku Sangyo Co., Ltd. and Kuraraycoal, made by Kuraray Chemical Co., Ltd. etc. can preferably be used.

The above-stated metallic salts should preferably include at least one of potassium chloride, potassium fluoride, silver nitrate, zinc chloride, magnesium chloride, and copper chloride (II) etc. The amount of metallic salt added to active carbon is acceptably 0.1 weight % to 50 weight % or more appropriately 0.5 weight % to 30 weight %.

The appropriate reaction temperature in the manufacturing method of the second invention is 200° C. to 600° C. or more appropriately 250° C. to 500° C. The reaction does progress very little under 200° C. and is liable to produce a large amount of unfavorable dissolved by-products over 600° C.

The contact time can be largely varied, but it is ordinarily 0.1 second to 300 seconds or more appropriately 0.5 second to 120 seconds.

The inventors have discovered that the contact of 1,1,1,2,3,3-hexafluoropropane in the gaseous state with active carbon which is treated with water or with active carbon under the presence of water causes a reaction to remove HF to produce 1,1,1,2,3-pentafluoropropene at high yields. The third invention has been achieved based on this discovery.

That is, the third invention relates to a method for manufacturing 1,1,1,2,3-pentafluoropropene characterized by the reaction to remove HF from 1,1,1,2,3,3-hexafluoropropane by means of the contact of 1,1,1,2,3,3-hexafluoropropane in the gaseous state with active carbon which is treated with water or with active carbon under the presence of water.

For the third invention, it is essential to make 1,1,1,2,3,3-hexafluoropropane in the gaseous state contact with active carbon which is treated with water or with active carbon under the presence of water. This is in practice a form of vapor phase reaction in which, for example, 1,1,1,2,3,3-hexafluoropropane in the gaseous state is made flow through a reaction tube filled with active carbon treated with water at a specific temperature, or 1,1,1,2,3,3-hexafluoropropane in the gaseous state is made flow through over active carbon under the presence of water. The methods of the vapor-phase reaction can be the fixed-bed reaction, the fluid-bed reaction and so on.

There are no particular restrictions in terms of kinds of active carbon to be used. The above-stated products can preferably be used.

There are no particular restrictions in terms of the method of water treatment on active carbon. The water immersion of active carbon and the vapor-phase steam treatment are acceptable. For the reaction procedure of flowing 1,1,1,2,3,3-hexafluoropropane concurrently with water, the amount of water content in the reaction gas should be ordinarily 1 ppm to 10%, or preferably 10 ppm to 5%.

The appropriate reaction temperature and contact time are 200° C. to 600° C. (or more appropriately 250° C. to 500° C.) and 0.1 second to 300 seconds (or more appropriately 0.5 second to 120 seconds), respectively, as in the above.

The inventors have discovered that the contact of 1,1,1,2,3,3-hexafluoropropane in the gaseous state with trivalent chromium oxide or partly fluorinated trivalent chromium oxide causes a reaction to remove HF to produce 1,1,1,2,3-pentafluoropropene at high yields. The fourth invention has been achieved based on this discovery.

That is, the fourth invention relates to a method for manufacturing 1,1,1,2,3-pentafluoropropene characterized by the reaction to remove HF by means of the contact of 1,1,1,2,3,3-hexafluoropropane in the gaseous state with trivalent chromium oxide or partly fluorinated trivalent chromium oxide.

The inventors have discovered that the contact of 1,1,1,2,3,3-hexafluoropropane in the gaseous state with either chromium (III) oxides or partly fluorinated chromium (III) oxides under the presence of oxygen causes a reaction to remove HF to produce 1,1,1,2,3-pentafluoropropene at high yields, and that the catalyst for this process tends to retain activity longer and have a longer life. The fifth invention has been achieved based on this discovery.

That is, the fifth invention relates to a method for manufacturing 1,1,1,2,3-pentafluoropropene characterized by the reaction to remove HF by means of the contact of 1,1,1,2,3,3-hexafluoropropane in the gaseous state with either chromium (III) oxides or partly fluorinated chromium (III) oxides under the presence of oxygen.

For the fifth invention, it is essential to make 1,1,1,2,3,3-hexafluoropropane in the gaseous state contact with either chromium (III) oxides or partly fluorinated chromium (III) oxides under the presence of oxygen. This is in practice a form of vapor phase reaction in which, for example, 1,1,1,2,3,3-hexafluoropropane in the gaseous state is made flow through a reaction tube filled with either chromium (III) oxides or partly fluorinated chromium (III) oxides at a specific temperature. The methods of the vapor-phase reaction can be the fixed-bed reaction, the fluid-bed reaction and so on.

For this invention, any preparation method of a catalyst comprising chromium (III) oxides or partly fluorinated chromium (III) oxides is acceptable. Chromium oxide can, for example, be prepared by reducing $CrO_3$ or by obtaining precipitate from a salt of $Cr^{3+}$.

A catalyst in the state of hydrate should be dried at 120° C. to 300° C. and then calcinated ordinarily at 300° C. to 600° C. or preferably at 350° C. to 450° C.

The treatment to fluorinate (or activate) a catalyst should be conducted ordinarily at 20° C. to 450° C. or preferably at 200° C. to 400° C. for the purpose. That fluorination can be conducted, for example, with hydrogen fluoride anhydride in the fluorination reaction system or by means of the heating treatment with fluorinated hydrocarbon. Partly fluorinated chromium (III) oxide can be obtained by heating a $CrF_3$ hydrate with oxygen.

The appropriate reaction temperature and contact time are 200° C. to 600° C. (or more appropriately 250° C. to 500° C.) and 0.1 second to 300 seconds (or more appropriately 0.5 second to 120 seconds), respectively, as in the above.

The concentration of oxygen present in said reaction of removing HF can be largely varied, but should ordinarily 0.005% to 20% of the total flow or preferably 0.01% to 10% of the total flow. An oxygen-containing mixed gas such as air can be used in the reaction process. In such a case, the gas concentration must comply with the above criterion figures for oxygen concentration.

The inventors have thoroughly studied production methods of 1,1,1,2,3-pentafluoropropane through vapor-phase catalytic reduction with a palladium catalyst, especially the methods that do not cause the problems mentioned in the above. As a result, they have discovered that hydrogenating 1,1,1,2,3-pentafluoropropene (particularly obtained through the reaction of removing HF caused by the contact of 1,1,1,2,3,3-hexafluoropropane in the gaseous state with active carbon as described in the above) as the raw material in the vapor or liquid phase under the presence of a palladium alloy catalyst at particularly 0° C. to 550° C. is an industrially easy manufacturing method of 1,1,1,2,3-pentafluoropropane with high yields to achieve the objective with high selectivity and high yields. The sixth invention has been achieved based on this discovery.

That is, the point of the sixth invention is in a method for manufacturing 1,1,1,2,3-pentafluoropropane characterized by the reduction of 1,1,1,2,3-pentafluoropropene with hydrogen under the presence of a hydrogenation catalyst consisting of palladium added with one or more metals selected from silver, copper, gold, tellurium, zinc, chromium, molybdenum, and thallium.

For the sixth invention, it is essential to add other metal(s) to palladium.

An alloy catalyst is generally considered to show the characteristics of the each constituent element according to its composition. For the invention, the amount of added metallic constituents to palladium should appropriately be 0.01 weight % to 500 weight %, or optimally 0.1 weight % to 300 weight % to take the advantage of the characteristics of palladium.

The acceptable amount of the carrying concentration of palladium alloy on various kinds of carriers is from 0.05% to 10%, but the recommended range is ordinarily 0.5% to 2%.

For the sixth invention, the appropriate carriers of palladium alloy catalysts are active carbon, alumina, silica gel, zirconia, titania, and so on.

The particle size of the carrier is preferably 0.1 mm to 100 mm although it has little effect on the reaction.

The ratio of hydrogen and the raw material in the 1,1,1,2,3-pentafluoropropene hydrogenation reaction can be largely varied. The reaction should, however, be ordinarily conducted with at least a stoichiometric amount of hydrogen. An amount of hydrogen, such as 4 mol or more, which is far more than the stoichiometric one can be used for the whole mol of the starting material.

The reaction should be conducted in the liquid or vapor phase. The methods of the vapor-phase reaction can be the fixed-bed reaction, the fluid-bed reaction and so on.

There are no restrictions on the reaction pressure so that the reaction can be conducted under a high pressure, a reduced pressure and the atmospheric pressure. It is preferable to conduct the reaction under a high pressure or the atmospheric pressure because the reduced pressure requires more complicated devices.

The appropriate reaction temperature is 0° C. to 550° C., and 50° C. to 450° C. for the vapor phase reaction.

For the vapor phase reaction, the contact time is ordinarily 0.1 second to 300 seconds or more appropriately 1 second to 30 seconds.

The material 1,1,1,2,3-pentafluoropropene used as the raw material for the method of the sixth invention can be synthesized through various methods.

Among those methods are: 1) the method of 1,1,1,2,3,3-hexafluoropropene (which is produced by hydrogenating hexafluoropropene) being reacted with an aqueous solution of KOH with a 70% to 80% concentration at 150° C. (Ann. Chim. (Italy) vol. 55, 850p, 1965); and 2) the method of being reacted with KOH in dibutylether (Izvest. Akad. Nauk S.S.S.R., Otdel. Khim. Nauk 1412p, 1960); and so on. Another method is: the method of removing HF with granular KCl in the vapor phase at 700° C. to product the desired product (Ann. Chim. (Italy) vol. 55, 850p. 1965).

As a cost-effective industrial manufacturing method with high yield, a reaction to remove HF from easily available 1,1,1,2,3,3-hexafluoropropane in the gaseous state by making contact with active carbon can be adopted.

Such methods for the vapor-phase reaction can be the fixed-bed reaction, the fluid-bed reaction and so on.

There are no particular restrictions in terms of kinds of active carbon to be used. A granular active carbon product, Shirasagi C, made by Takeda Yakuhin Kogyo Co., Ltd. and a coconut shell active carbon product, Yashicoal, made by Taihei Kagaku Sangyo Co., Ltd. can preferably be used.

The appropriate reaction temperature is 200° C. to 600° C. or more appropriately 250° C. to 500° C. It is not preferable that the above-stated reaction does progress very little under that temperature range and can produce a large amount of unfavorable dissolution by-products over that range.

The contact time with active carbon can be largely varied, but it is ordinarily 0.1 second to 200 seconds or more appropriately 0.5 second to 120 seconds.

The inventors have thoroughly studied production methods of 1,1,1,2,3-pentafluoropropane to solve the problems mentioned in the above. As a result, they have discovered that hydrogenating 1,1,1,2,3-pentafluoropropene as the raw material in the vapor phase under the presence of a rhodium catalyst brings about obtaining the target product at high yields. The seventh invention has been achieved based on this discovery.

That is, the seventh invention relates to a method for manufacturing 1,1,1,2,3-pentafluoropropane especially at a 97% or more high yield by means of the hydrogenation reaction on 1,1,1,2,3-pentafluoropropene as the starting material under the presence of a rhodium catalyst especially at 30° C. to 450° C.

For the seventh invention, it is essential to hydrogenate the material in the vapor phase by means of a rhodium catalyst. The methods of the vapor-phase reaction can be the fixed-bed reaction, the fluid-bed reaction and so on.

The rhodium catalysts are preferably supported on one or more carriers selected from active carbon, alumina, silica gel, titanium oxide, zirconia, and so on.

The particle size of the carrier is preferably 0.1 mm to 100 mm although it has little effect on the reaction.

The acceptable amount of the carrying concentration of rhodium is from 0.05 weight % to 10 weight %, but the recommended range is ordinarily 0.5 weight % to 5 weight %.

The appropriate reaction temperature is ordinarily 30° C. to 450° C. or more appropriately 70° C. to 250° C.

For the seventh invention, the ratio of hydrogen and the raw material for the 1,1,1,2,3-pentafluoropropene hydrogenation reaction can be largely varied. The reaction should, however, be ordinarily conducted with at least a stoichiometric amount of hydrogen. An amount of hydrogen, such as 2 mol or more, which is far more than the stoichiometric, one can be used for the whole mol of the starting material.

There are no restrictions on the reaction pressure so that the reaction can be conducted under a high pressure, a reduced pressure and the atmospheric pressure. It is preferable to conduct the reaction under a high pressure or the atmospheric pressure because the reduced pressure requires more complicated devices.

The contact time is ordinarily 0.1 second to 300 seconds or more appropriately 1 second to 30 seconds.

INDUSTRIAL APPLICABILITY

The present inventions make it possible to produce 1,1,1,2,3-pentafluoropropene, which is useful as an intermediate of useful compounds that can be substitutes for CFC and HCFC as refrigerants, blowing agents and cleaning agents, and as a monomer of macromolecule compounds from easily available 1,1,1,2,3,3-hexafluoropropane, by cost-effective industrial methods with high yields.

They also make it possible to produce 1,1,1,2,3-pentafluoropropane at high yields and high selectivities by reducing with hydrogen 1,1,1,2,3-pentafluoropropene under the presence of a rhodium catalyst or of a hydrogenation catalyst created by adding palladium with one or more metals selected from silver, copper, gold, tellurium, zinc, chromium, molybdenum, and thallium.

EMBODIMENTS

The inventions are more specifically explained with their embodiments hereunder.

Embodiment 1

20 cc of granular active carbon (Shirasagi C made by Takeda Yakuhin Kogyo Co., Ltd.) was filled into an SUS316 reaction tube of 2 cm inner diameter and 40 cm length and the tube was heated in an electric furnace at 430° C. while nitrogen gas was flowed through the tube. After 2 hours of the heating at that temperature, 1,1,1,2,3,3-hexafluoropropane was flowed through the tube at 20 cc/min, replacing nitrogen gas. The gas from the tube outlet was analyzed by gas chromatography after being washed with water and then dried with calcium chloride. Table 1 shows the results.

Embodiment 2

The similar procedures to those in Embodiment 1 was conducted with 20 cc of coconut shell active carbon (Yashicoal made by Taihei Kagaku Sangyo Co., Ltd.) filled in the same kind of reaction tube that was heated at 450° C. Table 1 shows the results.

TABLE 1

| | Embodiment 1 | Embodiment 2 |
| --- | --- | --- |
| Conversion (%) | 60.9 | 83.7 |
| Selectivity of 1,1,1,2,3-pentafluoropropene * (%) | 90.5 | 96.9 |

* Selectivity: % of the mixture of E and Z of 1,1,1,2,3-pentafluoropropene is shown.

The above results demonstrate that reaction according to the present inventions can produce the desired product on a cost-effective and high-yield basis.

Moreover, 20 cc of a palladium catalyst carried by alumina with a concentration of 0.5% was filled in an SUS316 reaction tube of 2 cm inner diameter and 40 cm length and the tube was heated in an electric furnace at 80° C. while nitrogen gas was flowed through it. After the tube was heated up to a given temperature, gaseous 1,1,1,2,3-pentafluoropropene, which had been vaporized in advance, was introduced into the tube at 57 cc/min with hydrogen introduced at 114 cc/min. The reaction temperature was maintained at 80° C. The produced gas (1,1,1,2,3-pentafluoropropane) was analyzed by gas chromatography after being washed with water and then dried with calcium chloride. The results were excellent with 100% of reactivity and 99% of selectivity.

Embodiment 3

25 cc of aqueous solution containing 0.95 g of KCl added with 10 g of Yashicoal M was stirred for 4 hours at 50° C. After water was distilled away under reduced pressure, it was dried at 120° C. for 24 hours. The resulted 8 g of catalyst was filled into an SUS316 reaction tube of 2 cm inner diameter and 40 cm length. Then the tube was heated in a electric furnace at 450° C. while nitrogen gas was flowed through the tube. 1,1,1,2,3,3-hexafluoropropane was flowed through the tube at 24 cc/min, replacing nitrogen gas. The gas from the tube outlet was analyzed by gas chromatography after being washed with water and then dried with calcium chloride. Table 2 shows the results.

Embodiment 4

25 cc of aqueous solution containing 0.74 g of KF added with 10 g of Yashicoal M was stirred for 4 hours at 50° C. After water was distilled away under reduced pressure, it was dried for 24 hours at 120° C. The resulted 8 g of catalyst was filled into the same kind of reaction tube as Embodiment 3. The reaction was conducted by flowing 1,1,1,2,3,3-hexafluoropropane through the tube at 24 ml/min at a reaction temperature of 450° C. Table 2 shows the results.

Embodiment 5

25 cc of aqueous solution containing 0.79 g of AgNO$_3$ added with 10 g of Yashicoal M was stirred for 4 hours at 50°

C. After water was distilled away under reduced pressure, it was dried for 24 hours at 120° C. The resulted 8 g of catalyst was filled into the same kind of reaction tube as Embodiment 3. The reaction was conducted by flowing 1,1,1,2,3,3-hexafluoropropane through the tube at 32 ml/min at a reaction temperature of 450° C. Table 2 shows the results.

Embodiment 6

25 cc of aqueous solution containing 1.3 g of $CuCl_2$ added with 10 g of Yashicoal M was stirred for 4 hours at 50° C. After water was distilled away under reduced pressure, it was dried for 24 hours at 120° C. The resulted 8 g of catalyst was filled into the same kind of reaction tube as Embodiment 3. Then a similar operation was performed, that is, the reaction was conducted by flowing 1,1,1,2,3,3-hexafluoropropane through the tube at 32 cc/min at a reaction temperature of 450° C. Table 2 shows the results.

Embodiment 7

25 cc of aqueous solution containing 1.95 g of $MgCl_2$ added with 10 g of Yashicoal M was stirred for 4 hours at 50° C. After water was distilled away under reduced pressure, it was dried for 24 hours at 120° C. The resulted 8 g of catalyst was filled into the same kind of reaction tube as Embodiment 3. The reaction was conducted by flowing 1,1,1,2,3,3-hexafluoropropane through the tube at 24 cc/min at a reaction temperature of 450° C. Table 2 shows the results.

Embodiment 8

8 g of Yashicoal M was filled in an SUS316 reaction tube of 2 cm inner diameter and 40 cm length. Then the tube was heated in an electric furnace at 400° C. while nitrogen gas was flowed through the tube.

Then 1,1,1,2,3,3-hexafluoropropane containing 4000 ppm of water was flowed through the tube at 24 cc/min, replacing nitrogen gas. The gas from the tube outlet was analyzed by gas chromatography after being washed with water and then dried with calcium chloride. Table 3 shows the results.

Embodiment 9

8 g of Yashicoal M was filled in an SUS316 reaction tube of 2 cm inner diameter and 40 cm length. Then the tube was heated in an electric furnace at 300° C. while water steam was flowed at 50 cc/min through the tube for 2 hours.

Then 1,1,1,2,3,3-hexafluoropropane was flowed through the tube at 24 cc/min at 400° C., replacing water steam. The gas from the tube outlet was analyzed by gas chromatography after being washed with water and then dried with calcium chloride. Table 3 shows the results.

Embodiment 10

Chromium hydroxide prepared from an aqueous solution of chromium nitrate and aqueous ammonia was filtrated, washed with water, and dried at 100° C. The resulted material was shaped into a cylinder of 3 mm inner diameter and 3 mm height by means of a tapping forming machine. The obtained catalyst was filled into a Hastelloy C reaction tube before the reaction and was activated by heating it at a constant temperature 400° C. in a nitrogen gas flow for 1 hour. Then, after the temperature was lowered down to 200° C., the catalyst was fluorinated by treating it with a supply of hydrogen fluoride anhydride diluted with $N_2$ for 5 hours.

10 g of the prepared catalyst was filled into a Hastelloy C reaction tube of 2 cm inner diameter and 40 cm length and the tube was heated in an electric furnace at 350° C. while flowing nitrogen gas through it.

Then 1,1,1,2,3,3-hexafluoropropane was flowed through the tube at 30 cc/min, replacing nitrogen gas. The gas from the tube outlet was analyzed by gas chromatography after being washed with water and then dried with calcium chloride. Table 4 shows the results.

Embodiment 11

10 g of the catalyst prepared according to the procedures in Embodiment 10 before the hydrogen fluoride anhydride treatment was filled into a Hastelloy C reaction tube of 2 cm inner diameter and 40 cm length and the tube was heated in an electric furnace at 400° C. while nitrogen gas was flowed through it.

Then 1,1,1,2,3,3-hexafluoropropane was flowed through the tube at 40 cc/min, replacing nitrogen gas. The gas from the tube outlet was analyzed by gas chromatography after being washed with water and then dried with calcium chloride. Table 4 shows the results.

Embodiment 12

Chromium hydroxide prepared from an aqueous solution of chromium nitrate and aqueous ammonia was filtrated, washed with water, and dried at 100° C. The resulted material was shaped into a cylinder of 3 mm diameter and 3 mm height by means of a tapping forming machine. The obtained catalyst was filled into a Hastelloy C reaction tube before the reaction and was heated at a constant temperature 400° C. in a nitrogen gas flow for 1 hour. Then, after the temperature was lowered down to 200° C., the catalyst was activated by treating it with a supply of hydrogen fluoride anhydride for 1 hours.

20 g of the prepared catalyst was filled into a Hastelloy C reaction tube of 2 cm inner diameter and 40 cm length and the tube was heated in an electric furnace at 350° C. while flowing nitrogen gas through it.

Then 1,1,1,2,3,3-hexafluoropropane was flowed through the tube at 57 cc/min with oxygen flowed at 3 cc/min, replacing nitrogen gas. The gas from the tube outlet was analyzed by gas chromatography after being washed with water and then dried with calcium chloride. Table 5 shows the conversion rate and selectivity 1 hour after the start of the reaction and those 100 hours after that.

Embodiment 13

20 g of the catalyst prepared according to the procedures in Embodiment 12 was filled into a Hastelloy C reaction tube of 2 cm inner diameter and 40 cm length and the tube was heated in an electric furnace at 350° C. while nitrogen gas was flowed through it.

Then 1,1,1,2,3,3-hexafluoropropane was flowed through the tube at 54 cc/min with air flowed at 6 cc/min, replacing nitrogen gas. The gas from the tube outlet was analyzed by gas chromatography after being washed with water and then dried with calcium chloride. Table 5 shows the conversion rate and selectivity 1 hour after the start of the reaction and those 100 hours after that.

Embodiment 14

20 g of the catalyst prepared according to the procedures in Embodiment 12 was filled into a Hastelloy C reaction tube of 2 cm inner diameter and 40 cm length and the tube was heated in an electric furnace at 350° C. while nitrogen gas was flowed through it.

Then 1,1,1,2,3,3-hexafluoropropane was flowed through the tube at 60 cc/min, replacing nitrogen gas. The gas from the tube outlet was analyzed by gas chromatography after being washed with water and then dried with calcium chloride. Table 5 shows the conversion rate and selectivity 1 hour after the start of the reaction and those 100 hours after that.

TABLE 2

|  | Conversion (%) | Selectivity * (%) |
|---|---|---|
| Embodiment 3 | 79.5 | 98.2 |
| Embodiment 4 | 85.7 | 97.5 |
| Embodiment 5 | 70.5 | 96.9 |
| Embodiment 6 | 65.5 | 97.0 |
| Embodiment 7 | 68.7 | 97.0 |

* Selectivity: % of the mixture of E and Z of 1,1,1,2,3-pentafluoropropene is shown. (The same applies hereinafter.)

TABLE 3

|  | Conversion (%) | Selectivity (%) |
|---|---|---|
| Embodiment 8 | 75.2 | 97.8 |
| Embodiment 9 | 75.0 | 97.5 |

TABLE 4

|  | Conversion (%) | Selectivity (%) |
|---|---|---|
| Embodiment 10 | 95.1 | 99.3 |
| Embodiment 11 | 90.0 | 99.2 |

TABLE 5

|  | 1 hour after the reaction started | | 100 hours after the reaction started | |
|---|---|---|---|---|
|  | Conversion (%) | Selectivity (%) | Conversion (%) | Selectivity (%) |
| Embodiment 12 | 85.4 | 99.7 | 85.1 | 99.6 |
| Embodiment 13 | 85.3 | 99.8 | 85.1 | 99.6 |
| Embodiment 14 | 85.1 | 99.8 | 45.2 | 99.5 |

The results of the embodiments described above clearly demonstrate that 1,1,1,2,3-pentafluoropropene is obtained from easily available 1,1,1,2,3,3-hexafluoropropane by a cost-effective industrial method with high yields in accordance with the present inventions.

Embodiment 15

Palladium catalyst carried by active carbon at a 0.5% concentration was added to an aqueous solution of $CuCl_2$ of 0.1% concentration as Cu to the active carbon and was dropped with 0.2 ml of formalin. After the resulted substance was heated at 50° C. for 5 hours, it was distilled to remove water under reduced pressure and then it was dried for 24 hours at 100° C.

18 cc of the obtained catalyst was filled into an SUS316 reaction tube of 2 cm inner diameter and 40 cm length, and the tube was heated in an electric furnace at 350° C. for 3 hours while hydrogen gas was flowed through it at 40 cc/min. Then, after the temperature was lowered down to an appropriate level, gaseous 1,1,1,2,3-pentafluoropropene, which had been vaporized, was introduced into the tube at 20 cc/min with hydrogen introduced at 40 cc/min. The reaction temperature was 80° C. This 1,1,1,2,3-pentafluoropropene was that which was made in Embodiment 2.

The produced gas, which contains 1,1,1,2,3-pentafluoropropane, was analyzed by gas chromatography after being washed with water and then dried with calcium chloride. Table 6 shows the results.

Embodiment 16

Palladium catalyst carried by active carbon at a 0.5% concentration was added with silver by the use of $AgNO_3$ at a 0.1% concentration as Ag to prepare an alloy catalyst in accordance with the preparation procedures described in Embodiment 15. Then the same reaction as Embodiment 15 was conducted. Table 6 shows the results.

Embodiment 17

Palladium catalyst carried by active carbon at a 0.5% concentration was added with tellurium by the use of $TeCl_2$ at a 0.1% concentration as Te to prepare an alloy catalyst in accordance with the preparation procedures described in Embodiment 15. Then the same reaction as Embodiment 15 was conducted. Table 6 shows the results.

Embodiment 18

Palladium catalyst carried by active carbon at a 0.5% concentration was added with gold by the use of $AuCl_3$ at a 0.1% concentration as Au to prepare an alloy catalyst in accordance with the preparation procedures described in Embodiment 15. Then the same reaction as Embodiment 15 was conducted. Table 6 shows the results.

Embodiment 19

Palladium catalyst carried by active carbon at a concentration was added with zinc by the use of $ZnCl_2$ at a 2% concentration as Zn to prepare an alloy catalyst in accordance with the preparation procedures described in Embodiment 15. The obtained alloy catalyst was filled into an SUS316 reaction tube of 2 cm inner diameter and 40 cm length, and the tube was heated in an electric furnace at 350° C. while hydrogen gas was flowed through it at 40 cc/min.

Then, after the temperature was lowered down to a specific level, gaseous 1,1,1,2,3-pentafluoropropene, which had been vaporized, was introduced into the tube at 40 cc/min with hydrogen introduced at 80 cc/min. The reaction temperature was 100° C.

The produced gas was analyzed by gas chromatography after being washed with water and then dried with calcium chloride. Table 6 shows the results.

Embodiment 20

Palladium catalyst carried by active carbon at a 0.5% concentration was added with chromium by the use of $Cr(NO_3)_3 \cdot 9H_2O$ at a 2% concentration as Cr to prepare an alloy catalyst in accordance with the preparation procedures described in Embodiment 15. 17 cc of the obtained alloy catalyst was filled into an SUS316 reaction tube of 2 cm inner diameter and 40 cm length, and the tube was heated in an electric furnace at 400° C. while hydrogen gas was flowed through it.

Then, after the temperature was lowered down to a specific level, gaseous 1,1,1,2,3-pentafluoropropene, which had been vaporized, was introduced into the tube at 30 cc/min with hydrogen introduced at 60 cc/min. The reaction temperature was 100° C.

The produced gas was analyzed by gas chromatography after being washed with water and then dried with calcium chloride. Table 6 shows the results.

Embodiment 21

Palladium catalyst carried by active carbon at a 0.5% concentration was added with thallium by the use of $TlCl_3$ at a 2% concentration as Tl to prepare an alloy catalyst in accordance with the preparation procedures described in Embodiment 15. 15 cc of the obtained alloy catalyst was filled into an SUS316 reaction tube of 2 cm inner diameter and 40 cm length, and the tube was heated in an electric furnace at 350° C. while hydrogen gas was flowed through it at 40 cc/min.

Then, after the temperature was lowered down to a specific level, gaseous 1,1,1,2,3-pentafluoropropene, which had been vaporized, was introduced into the tube at 40 cc/min with hydrogen introduced at 80 cc/min. The reaction temperature was 150° C.

The produced gas was analyzed by gas chromatography after being washed with water and then dried with calcium chloride. Table 6 shows the results.

Embodiment 22

Palladium catalyst carried by active carbon at a 0.5% concentration was added with molybdenum by the use of $(NH_4)_6Mo_7O_{24} \cdot 4H_2O$ at a 2% concentration as Mo to prepare an alloy catalyst in accordance with the preparation procedures described in Embodiment 15. 15 cc of the obtained alloy catalyst was filled into an SUS316 reaction tube of 2 cm inner diameter and 40 cm length, and the tube was heated in an electric furnace at 350° C. while hydrogen gas was flowed through it at 40 cc/min.

Then, after the temperature was lowered down to a specific level, gaseous 1,1,1,2,3-pentafluoropropene, which had been vaporized, was introduced into the tube at 30 cc/min with hydrogen introduced at 60 cc/min. The reaction temperature was 120° C.

The produced gas was analyzed by gas chromatography after being washed with water and then dried with calcium chloride. Table 6 shows the results.

Embodiment 23

Palladium catalyst carried by powdered active carbon at a 5% concentration was added with an aqueous solution of $AgNO_3$ of 1% concentration against the active carbon and then was added with 0.2 ml of formalin. After the resulted substance was heated for 5 hours at 50° C., it was distilled to remove water under reduced pressure. Analysis showed that the obtained catalyst contained 54% of water.

1 g of the obtained catalyst was put in an SUS316 autoclave of 200 cc. After the nitrogen substitution, 10 g of 1,1,1,2,3-pentafluoropropene was introduced into the autoclave. Then hydrogen gas was introduced until its amount reaches 9 kg/cm² at a room temperature while stirring. Hydrogen gas was added each time it was consumed and the reaction was maintained until hydrogen gas was not consumed any more. The reaction temperature was held at 25° C. or under.

After the reaction finished, the reaction liquid was analyzed by gas chromatography. Table 6 shows the results.

TABLE 6

| Embodiment No. | Conversion (%) | Selectivity (%) |
|---|---|---|
| 15 | 99 | 98 |
| 16 | 99 | 98 |
| 17 | 99 | 96 |
| 18 | 99 | 98 |
| 19 | 98 | 97 |
| 20 | 99 | 97 |
| 21 | 98 | 96 |
| 22 | 98 | 96 |
| 23 | 99 | 98 |

The above results demonstrate that hydrogenation reaction according to the present inventions can produce the desired product at high conversion and high selectivity.

Embodiment 24

10 cc of a rhodium catalyst carried by alumina at 0.5% concentration was filled in an SUS316 reaction tube of 2 cm inner diameter and 40 cm length. Then the tube was heated in an electric furnace at 80° C. while nitrogen gas was flowed through the tube.

After the tube temperature reached a specific level, gaseous 1,1,1,2,3-pentafluoropropene, which had been vaporized, was introduced at 26.7 cc/min with hydrogen introduced at 55.3 cc/min. The reaction temperature was held at 80° C. The produced gas was analyzed by gas chromatography after being washed with water and then dried with calcium chloride. Table 7 shows the results.

Embodiment 25

18 cc of a rhodium catalyst carried by active carbon at 0.5% concentration was filled into the same reaction device as Embodiment 24. Then the device was heated in an electric furnace at 120° C. while nitrogen gas was flowed through the tube.

After the tube temperature reached a specific level, gaseous 1,1,1,2,3-pentafluoropropene, which had been vaporized, was introduced at 40 cc/min with hydrogen introduced at 80 cc/min. The reaction temperature was held at 120° C. The produced gas was analyzed by gas chromatography after being washed with water and then dried with calcium chloride. Table 7 shows the results.

TABLE 7

| Embodiment No. | Conversion (%) | Selectivity (%) |
|---|---|---|
| 24 | 100 | 99 |
| 25 | 100 | 99 |

The above results demonstrate that reaction according to the present inventions can produce the desired product 1,1,1,2,3-pentafluoropropane at high yields.

We claim:

1. A method for producing 1,1,1,2,3-pentafluoropropene by the selective removal of hydrogen fluoride from 1,1,1,2,3,3-hexafluoropropane which comprises contacting gaseous 1,1,1,2,3,3-hexafluoropropane with active carbon.

2. A method according to claim 1, wherein the gaseous 1,1,1,2,3,3-hexafluoropropane is contacted with the active carbon at 200°–600° C.

3. A method according to claim 1, wherein the active carbon has one or more metallic salts added thereto.

4. A method according to claim 3, wherein the metallic salts are salts of potassium, silver, zinc, copper or magnesium.

5. A method according to claim 1, wherein the active carbon is treated with water prior to contacting the active carbon with the gaseous 1,1,1,2,3,3-hexafluoropropane.

6. A method according to claim 1, wherein the gaseous 1,1,1,2,3,3-hexafluoropropane is contacted with the activated carbon in the presence of water.

7. A method for producing 1,1,1,2,3-pentafluoropropene by the selective removal of hydrogen fluoride from 1,1,1,2,3,3-hexafluoropropane which comprises contacting gaseous 1,1,1,2,3,3-hexafluoropropane with trivalent chromium oxide or partially fluorinated trivalent chromium oxide.

8. A method according to claim 7, wherein the gaseous 1,1,1,2,3,3-hexafluoropropane is contacted with the trivalent chromium oxide or partially fluorinated trivalent chromium oxide in the presence of oxygen.

9. A method for preparing 1,1,1,2,3-pentafluoropropane which comprises contacting gaseous 1,1,1,2,3,3-hexafluoropropane with active carbon, trivalent chromium oxide or partially fluorinated trivalent chromium oxide, to selectively remove hydrogen fluoride from the 1,1,1,2,3,3-hexafluoropropane to form 1,1,1,2,2,3-pentafluoropropene; and reducing the 1,1,1,2,3-pentafluoropropene with hydrogen in the presence of a hydrogenation catalyst comprising palladium and at least one metal selected from the group consisting of silver, copper, gold, tellurium, zinc, chromium, molybdenum and thallium.

10. A method according to claim 9, wherein the hydrogenation catalyst contains 0.01–500% of the at least one metal based on the weight of the palladium.

11. A method according to claim 9, wherein the 1,1,1,2,3-pentafluoropropene is reduced with at least a stoichiometric amount of hydrogen.

12. A method according to claim 10, wherein the 1,1,1,2,3-pentafluoropropene is reduced with hydrogen at a temperature of 0°–550° C.

13. A method according to claim 9, wherein the hydrogenation catalyst is supported on a carrier.

14. A method according to claim 13, wherein the carrier is at lease one carrier selected from the group consisting of active carbon, alumina, silica gel, titanium oxide and zirconia.

15. A method according to claim 14, wherein the carrier contains 0.05–10% by weight of the hydrogenation catalyst.

16. A method for preparing 1,1,1,2,3-pentafluoropropane which comprises reacting 1,1,1,2,3-pentafluoropropene in the vapor phase with hydrogen in the presence of a rhodium catalyst.

17. A method according to claim 16, wherein the 1,1,1,2,3-pentafluoropropene is reacted with at least a stoichiometric amount of hydrogen.

18. A method according to claim 17, wherein the 1,1,1,2,3-pentafluoropropene is reacted with hydrogen at a temperature in the range of 30°–450° C.

19. A method according to claim 16, wherein the rhodium catalyst is supported on at least one carrier selected from the group consisting of active carbon, alumina, silica gel, titanium oxide and zirconia.

20. A method according to claim 19, wherein the carrier contains 0.05–10% by weight of the rhodium catalyst.

* * * * *